United States Patent [19]

Raghavan et al.

[11] Patent Number: 5,125,036
[45] Date of Patent: Jun. 23, 1992

[54] VIDEO BOND LEAD LOCATOR

[75] Inventors: Asuri Raghavan, Warrington; Satish Natu; Raymond Foran, both of Philadelphia, all of Pa.

[73] Assignee: Kulicke & Soffa Industries, Inc., Willow Grove, Pa.

[21] Appl. No.: 85,240

[22] Filed: Aug. 7, 1987

Related U.S. Application Data

[63] Continuation of Ser. No. 735,839, May 20, 1989, abandoned.

[51] Int. Cl.$^5$ .................................................. G06K 9/00
[52] U.S. Cl. ........................................... 382/8; 382/18; 382/48
[58] Field of Search ............... 382/8, 18, 22, 48; 358/101, 106, 107; 356/375, 387, 398; 364/489, 490, 491

[56] References Cited

U.S. PATENT DOCUMENTS

| | | | |
|---|---|---|---|
| 4,238,780 | 12/1980 | Doemens | 382/8 |
| 4,441,025 | 4/1984 | Berkin et al. | 382/8 |
| 4,442,542 | 4/1984 | Lin et al. | 382/8 |

Primary Examiner—Leo H. Boudreau
Attorney, Agent, or Firm—Woodcock Washburn Kurtz Mackiewicz & Norris

[57] ABSTRACT

An image processing system and method are used to ascertain the position of lead frame beams on a semiconductor lead frame prior to the formation of wire bonds to those lead frame beams. The lead frame beams are illuminated by a light source and light reflected from the lead frame beams is detected. Digital data representative of the reflected light is generated and stored in a memory. A control means defines corridors in that memory which are analyzed to define the position of the lead frame beams and to distinguish light reflected from the lead frame beams themselves from light reflected from interlead ceramic or glasslike material.

22 Claims, 7 Drawing Sheets

VIDEO BOND LEAD LOCATOR

This is a continuation of application Ser. No. 735,839, filed May 20, 1985 now abandoned.

FIELD OF THE INVENTION

The present invention relates, in general, to an image processing system and method and, in particular, the invention relates to an image processing system and method for precisely determining the location of the beams of an integrated circuit chip lead frame so that wires may be bonded to the beams of the lead frame by wire bonding apparatus.

BACKGROUND OF THE INVENTION

In the prior art, integrated circuit chips have been electrically coupled to lead frames by means of a plurality of wire bonds. These bonds are typically formed by wire bonding apparatus.

As the circuit density of integrated circuit chips has increased, the accurate positioning of a wire bonding head used to form wire bonds with respect to the various bonding pads of an integrated circuit chip has been more and more difficult. In U.S. Pat. No. 4,441,205-Berkin, which is assigned to the assignee of the present invention, a pattern recognition system is disclosed and claimed which alleviates the difficulties of positioning a wire bonding head with respect to the bonding pads of an integrated circuit chip. As chip density has continued to increase, however, a new problem has arisen.

As integrated circuit densities have continued to increase and the circuits have become more complex, the configuration of the lead frames which provide input and output to the chips has also become more and more complex. The lead frame beams to which wire bonds must be made have become increasingly smaller and more numerous and, therefore, more difficult to form wire bonds thereto. The decrease in lead frame beam size, however, is not the only problem. Another problem arises because the manufacturing tolerances of lead frames are such that the position of a given beam in a given lead frame configuration may vary from one lead frame to the next. The techniques employed in fabricating integrated circuit chips themselves are very precise and, therefore, the position of bonding pads on an integrated circuit chip do not vary significantly from one chip to the next. The techniques of forming lead frames, however, are relatively less precise and, therefore, the actual position of a given lead frame beam may vary from one lead frame to another. As chip densities have increased, therefore, the task of forming wire bonds to lead frame beams has grown more difficult because the target areas to which bonds are to be formed smaller than previously and the position of those target areas is variable.

Initially, the positioning of the wire bonding head with respect to a lead frame beam was done blindly. With blind bonding, the wire bonding apparatus simply assumed that the lead frame beam to which a wire bond was to be made was exactly where it was expected to be. Such an approach was suitable for relatively large sized lead frame beams. As lead frame beams decreased in size and chip densities increased however, such a technique was no longer applicable.

The next technique employed for the positioning of a wire bonding head with respect to a lead frame beam was manual. With this manual technique, the relative position of the lead frame beam was moved with respect to the wire bonding head by a human operator before the wire bond was formed. Such manual techniques, however, had very low throughput and were labor intensive.

In a third technique which has been employed, the position of the lead frame beam was adjusted with respect to the wire bonding head in accordance with the sensed position of the lead frame beam, the position being sensed by light reflected from the lead frame beam. With this third technique light from a light source was focused upon the lead frame. Light, reflected from the lead frame beam, was sensed by a light detector. The output from the light detector thus provided an indication of the lead frame beam position. The relative position of the lead frame was then varied with respect to the wire bonding head in response to the sensed position of the beam before the wire bond was formed.

At least two such reflected light techniques have been employed and both suffer from disadvantages, especially with certain types of integrated circuit lead packages. Lead packages fall into two categories. In the first category, after the lead frame is joined with respect to the integrated circuit chip by means of wire bonding, the chip and lead frame package are encapsulated in a thermoplastic material. Such packages are adaptable to techniques for beam lead positioning which employ reflected light because the reflectance of the lead frame beams in these packages is clearly distinguishable from that of the background. In a second category of integrated circuit packages, however, the lead frame is first encapsulated in a ceramic material and the integrated circuit chip is bonded to the ceramic encapsulated lead frame. Such packages are referred to as ceramic dual in line packages or cerdips. With cerdip packages, the reflectance of the integrated circuit beam is similar to the reflectance of the surface of the glass-like material found between the lead frame beams. Certain material located between the lead frame beams in such packages, sometimes referred to as interlead glass, has a reflectivity similar to that of the metal of the beams themselves. Because of this fact cerdip packages have been known to misinform those systems which use reflected light for sensing position, resulting in wire bonds being formed in the wrong location.

Since it is important for position sensing systems used with wire bonding apparatus to be suitable for use with both cerdip type integrated circuit packages which suffer from problems caused by the reflectance of interlead glass, as well as standard lead frames which do not include interlead glass, prior art position sensing systems have not been suitable.

In one reflected light position sensing system which has been sold by the assignee of the present invention, another difficulty, in addition to the reflectance problems caused by interlead glass, has been presented. In that system, each lead frame beam of a lead frame package was translated with respect to a light source and light detector until the position of that lead frame beam was precisely known. Thereafter, the position of the lead frame beam was adjusted with respect to a wire bonding head such that the wire bond would be formed at the appropriate location. Such a technique was found to result in undue intermittent motion of the lead frame with respect to the wire bonding apparatus. This intermittent motion imposed severe loads on the drive mechanism for the wire bonding head.

It would be desirable to provide an image processing system and method for a wire bonding apparatus which was capable of accurately positioning a lead frame with respect to a wire bonding head.

It would be further desirable to provide an image processing system and method for a wire bonding apparatus having the capability of reliably locating a large number of extremely small lead frame beams.

It would be still further desirable to provide an image processing system and method for a wire bonding apparatus having improved throughput over manual techniques.

It would be still further desirable to provide such an image processing system and method which, though employing reflected light, is capable of distinguishing between the reflectance caused by interlead glass of ceramic dual-in-line packages, and the lead frame beams themselves.

It would be still further desirable to provide such an image processing system and method which could accurately determine the position of a plurality of lead frame beams without the necessity of complex motions of the lead frame beams with respect to a wire bonding head so as to minimize inertial problems.

These and other objects of the present invention are achieved by a system and method for determining the position of leads on a semiconductor lead frame with respect to a wire bonding apparatus. In carrying out the method of the present invention, the lead frame is illuminated with light from a light source. Light reflected from the lead frame is sensed and digital data representing that reflected light is generated. The digital data so generated is stored in a memory. A control means defines a corridor in that memory, the corridor having a length and a width. A first signature of data within that corridor is obtained, the first signature being a widthwise summation of data at each point along the length of the corridor. First order derivatives of the first signature along the length of the corridor are determined and stored in a first array. The first array is scanned to determine those points along the corridor having first order derivatives typical of lead boundaries. Other first order derivatives are deleted from the array. The first array is scanned by the control means to determine regions between candidate lead boundaries, the positions of such regions being stored in a second array. The second array is scanned to determine whether the regions between candidate lead boundaries have a dimension which exceeds the minimum dimension of leads.

In accordance with an important aspect of the present invention, if the semiconductor lead frame under consideration is a ceramic dual-in-line package, the method of the present invention further includes the step of defining a series of second corridors orthogonal to the first corridor. These second corridors are located at points along the first corridor determined to be candidate lead boundaries. Second signatures are obtained in each of the second corridors and the second signatures are analyzed to distinguish leads from specular reflection of light from interlead material.

BRIEF DESCRIPTION OF THE DRAWINGS

The present invention will be better understood if reference is made to the accompanying drawings, in which.

DESCRIPTION OF THE PREFERRED EMBODIMENTS

Figure 1:
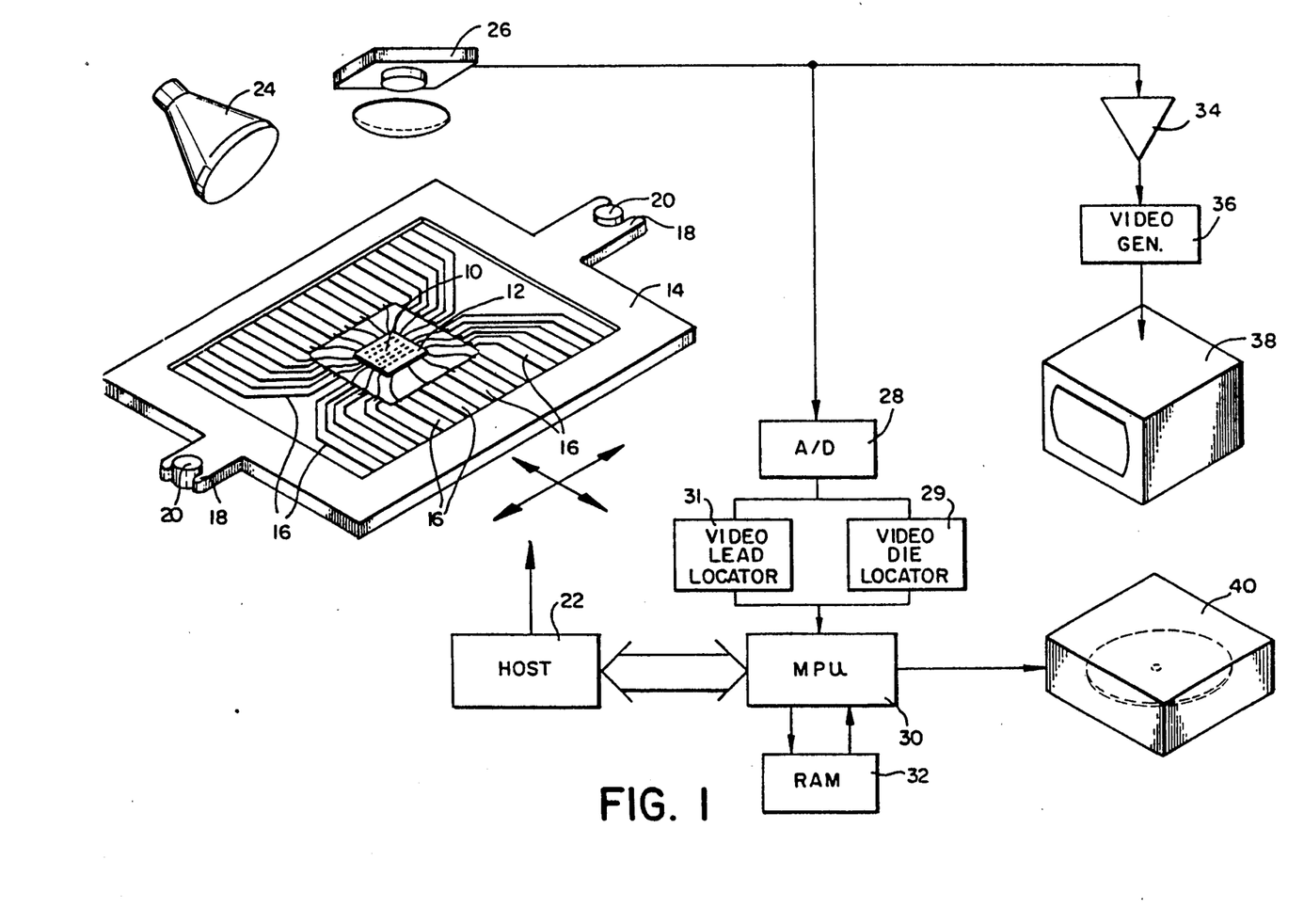
FIG. 1 is a schematic view of the overall system of which the image processing system of the present invention is a part.

FIG. 1 shows a schematic view of an overall system for bonding wire leads to an integrated circuit chip and also to a lead frame. The portion of the overall system of FIG. 1 for forming wire bonds to a chip is set forth and described in detail in U.S. Pat. No. 4,441,205 which is assigned to the assignee of the present invention which is incorporated herein by reference. The portion of the overall system of FIG. 1 for bonding such wire leads to the beams of an integrated circuit lead frame is the subject of the present invention. In accordance with the overall system a chip 10 provided with bonding pads 12 is affixed to an integrated circuit lead frame indicated generally at 14. This lead frame 14 includes a plurality of beams 16, which are large enough so that they can be attached to conventional terminals, such as in-line pins, and the like. The lead frame 14 is shown schematically as provided with means 18 adapted for mating with index means 20 disposed on a host bonding machine. The host machine is provided with a table on which the index means 20 is disposed; the table is adapted to be movable in orthogonal directions, as indicated by the arrows, under the control of the host controller indicated generally at 22. The bonding machine further includes means for attaching wire leads not only to the bonding pads 12 of the integrated circuit chip 10 but also to the beams 16 of the lead frame 14 in a manner known in the prior art which need not be further discussed here.

What is relevant here is the means of indicating to the host controller 22 where precisely the chip, and hence the bonding pads 12, as well as the lead frame beams 16 are with respect to the host machine. The apparatus for performing this operation comprises a source of light 24 and optical and camera means 26 which may comprise a video tube, a vidicon, a solid state sensor or the like, adapted to sweep in raster-fashion over an area corresponding to the area viewed. The analog signal output of the camera means 26 is converted in an analog-todigital converter 28 to digital representations of the light intensity falling on the camera at corresponding locations in known fashion. Typically the field of the view of the camera 26 is divided into an N by M array of square areas on its surface, referred to as picture elements, or "pixels", and a digital number representative of the light intensity or gray level within that area is provided for each of the N×M pixels. In a preferred embodiment of the present invention a 4-bit word providing 16 stages of light density is used to represent each pixel; the pixels are 0.00025" square, that is, there are four pixels per mil.

The digitized samples from the A/D converter 28 are supplied to a video die locator circuit 29 which is both described in detail and claimed in U.S. Pat. No. 4,441,205 mentioned above. The digitized samples are also supplied to a video lead locator circuit 31 in accordance with the image processing system of the present invention. The output of both the video die locator circuit 29 and the video lead locator circuit 31 are supplied to a microprocessor unit 30, which is further coupled to access memory means 32. A buffer amplifier 34 may also be provided to drive a video generator 36 which supplies a television screen 38 with a picture of what is viewed by the camera 26 to assist in the operator location of the chip 10 and lead frame 14 with respect to reference locations during the teach operation, as will be outlined below. The microprocessor 30 may also feed on-line storage means such as a floppy disk drive shown schematically at 40 for storage of information generated according to the method of the invention, as will be discussed in detail below.

Figure 2:
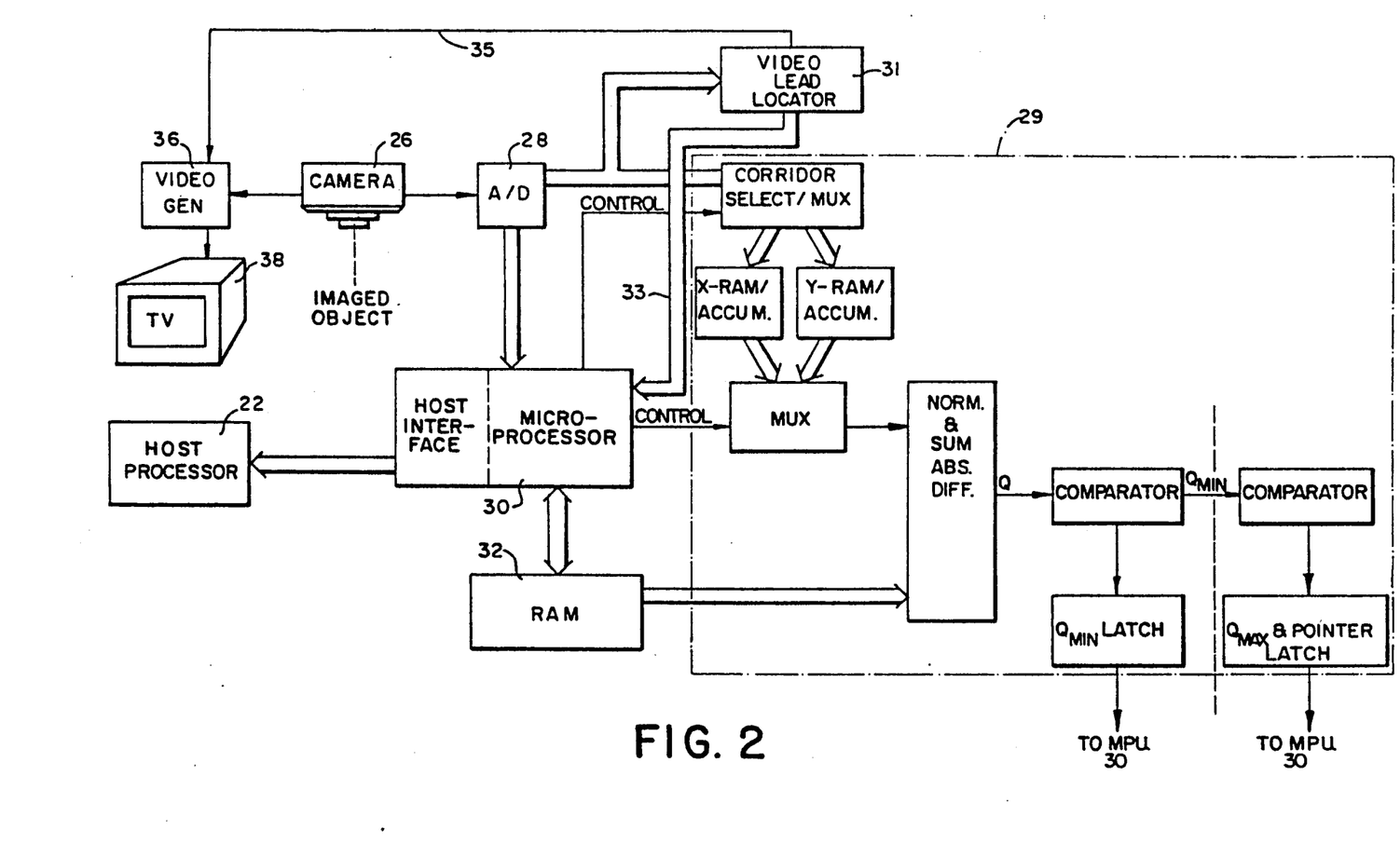
FIG. 2 is a more detailed block diagram of the overall system shown in FIG. 1 including portions of the pattern recognition system set forth and described in detail in U.S. Pat. No. 4,401,205 which is assigned to the assignee of the present invention as well as a portion which includes the image processing system of the present invention.

Referring now to FIG. 2, the overall system shown in FIG. 1 will be described in further detail. As shown in FIG. 2, image data detected by a camera 26 is directed to analog digital converter 28 and from the analog digital converter 28 to the video lead locator circuit 31 of the image processor of the present invention and also to the video die locator circuit 29 described in connection with U.S. Pat. No. 4,441,205 mentioned above. The video die locator circuit 29 yields an output directed to the microprocessor unit 30 which provides accurate location of the bonding pads 12 of integrated circuit chip 10. The manner in which this is accomplished is described in connection with the foregoing patent. The video lead locator circuit 31 of the present invention also provides an output to the microprocessor unit 30 along output bus 33. The output from the video lead locator circuit 31 provides an indication as to the accurate position of the various beams 16 of the lead frame 14. This output is further directed via line 35 to the video generator 36 for display on the monitor 38 to the operator.

Figure 3:
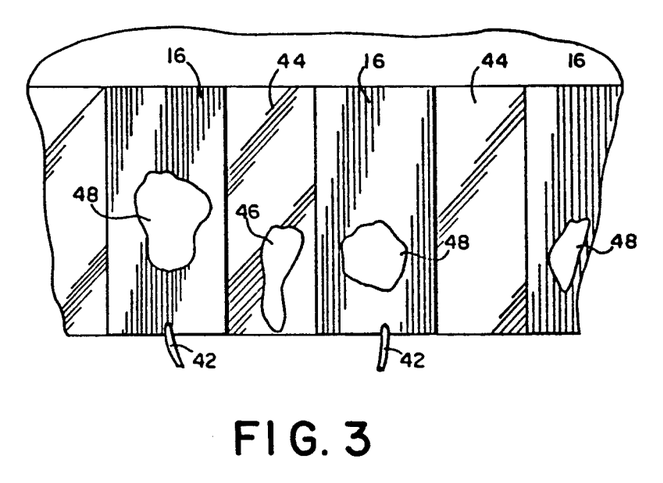
FIG. 3 is an exploded view of a portion of a typical lead frame showing a dark reflective patch of a particular lead frame beam and the specular reflection of interlead glass at one location.

Referring now to FIG. 3, the layout of a portion of a typical lead frame 14 will be seen. Bonds are formed between the bonding pads on the integrated circuit chip and one end of the wire 42. The other end of the wire 42 is bonded to the beams 16 of the lead frame 14. The lead frame 14 as shown in FIG. 3 is a ceramic dual-in-line package and, accordingly, situated between the beams 16 is an interlead ceramic material 44. Typically, formed on the surface of such ceramic material 44 is a glassy layer sometimes referred to as interlead glass. Interlead glass typically has a reflectivity similar to the reflectivity of the lead frame beams 16. Accordingly, as shown in FIG. 3 areas of specular reflection such as at 46 may be seen which appear to the camera 26 as being similar to the lead frame beams 16. It is important in determining the position of the lead frame beams 16 to distinguish between areas of specular reflection such as 46 and adjacent lead frame beams 16 so as to avoid the formation of wire bonds on the areas of specular reflection 46.

Also, as shown in FIG. 3, dark patches such as 48 are sometimes detected by the camera 26 on the surface of lead frame beams 16. These dark patches 48 are believed to be caused by irregularities in the surface of the metallization of the lead frame beams 16. It is important in determining the precise location of lead frame beams 16 that an image processing system be able to distinguish between the lead frame beams 16 themselves and the surrounding interlead material 44 despite the presence of dark spots or patches on the beams such as 48 as shown. In accomplishing this objective utilizing the system generally described in FIG. 1 and more fully shown in FIG. 2, the video lead locator circuit 31 may comprise hardware shown in FIG. 4 which follows the process described in connection with FIGS. 6–9 below.

Figure 4:
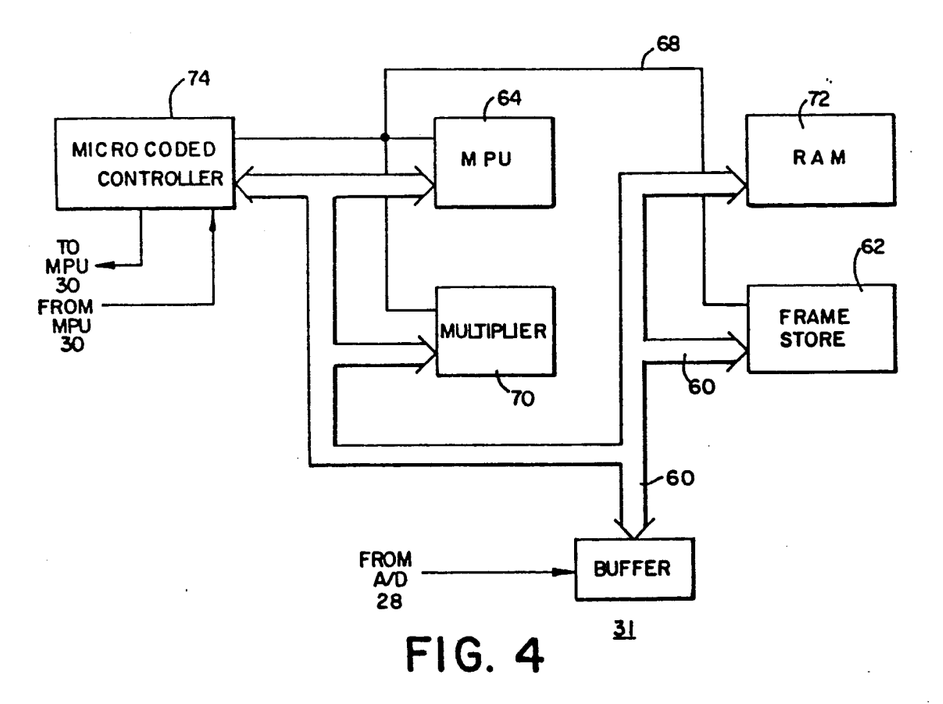
FIG. 4 is a detailed block diagram of the video lead locator circuit of the image processing system of FIG. 1, which determines the precise location of the lead frame beams shown in FIG. 3.

The hardware of the video lead locator 31 may be seen in FIG. 4. Digital input from the analog to digital converter 28 is directed through a buffer 59 to input bus 60. Digital input is directed via input bus 60 to a memory 62 at which it is stored in raster scan order on a frame-by-frame basis. A microprocessor unit 64 is provided which is coupled to the memory 62 via data bus 66 and via address and control line 68. The microprocessor controller 64 operates upon the digital data stored in the memory 62 in a manner which will be described below to discriminate beams 16 from specular reflection such as 46 and dark patches 48 on those beams. In accordance with the preferred aspect of the present invention, a separate multiplication unit 70 is provided which is coupled to microprocessor 64 by the data bus 66. In addition, a 4K by 16 random access memory 72 is further coupled to microprocessor 64 by data bus 66. The multiplication unit 70 and the random access memory 72 are both desirable but not necessary to increase the speed of the requisite computations. In addition, in accordance with the preferred embodiment of the present invention, an additional micro-coded controller 74 is provided which is coupled between the microprocessor 64 and the microprocessor 30. Micro-coded controller 74 controls the operation of microprocessor 64. The microprocessor unit 30 provides coordination and communication for outputting results obtained by the video lead locator circuit 31 to the host controller 22.

Figure 5:
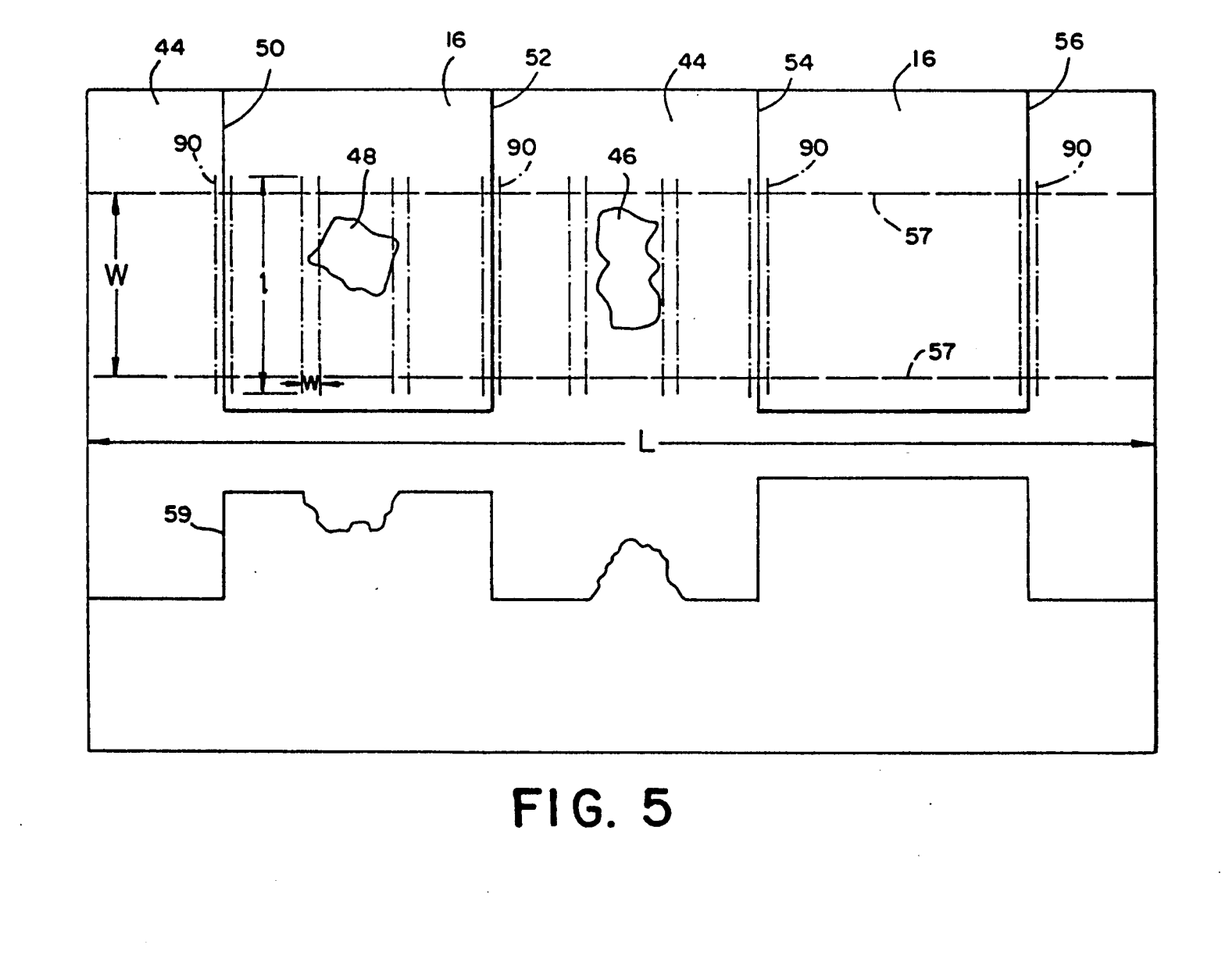
FIG. 5 shows how the digital representations of the lead frame beams, picture elements or "pixels" may be summed by the video lead locator circuit of FIG. 4 to yield unique signatures in a defined corridor in accordance with the system and method of the present invention.
Figure 6:
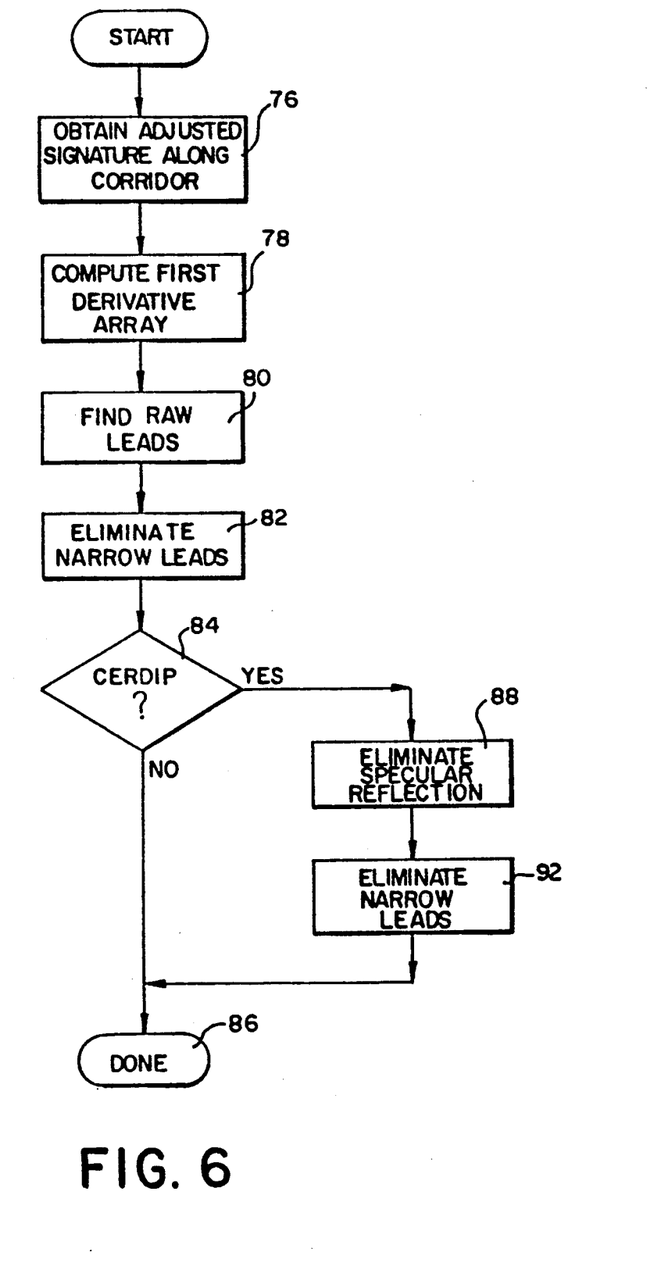
FIG. 6 is a flow chart of the lead location operation of the image processor system of FIG. 1.

Referring now to FIGS. 5–6, the method of operation of the microprocessor 64 will be described. FIG. 5 represents the video image received by the camera 26 for a given field of view. As shown in FIG. 5, lead frame beams 16 are separated by interlead ceramic material 44. Interlead specular reflections 46 are present as well as a dark patch 48 on one lead frame beam 16. The video bond lead locator circuit 31 of the present invention reliably determines the edges 50, 52, 54, and 56 of the lead frame beams 16 and is unaffected by the presence of dark patches such as 48 or specular reflections such as 46.

As shown in FIG. 5, the microprocessor 64 first defines a corridor depicted by dashed lines 57 in the frame storage memory 62. The corridor 57 has a width W and a length L. It is preferred that the corridor have a width W which is sufficiently large as to exceed the width of the largest specular reflection such as specular reflection 46 shown in FIG. 5. The length L of the first corridor typically equals the length of the field of view of the camera 26.

Referring now to FIG. 6, it will be seen that the first step in the present method is the obtaining of an adjusted signature along the corridor 57. In carrying out this teaching, a first signature of the data within the corridor 57 is obtained. This first signature, which may be referred to as "SIGN", is a widthwise summation of data at each point along the length L of the corridor 57. A plot showing this first signature, SIGN, for the corridor of FIG. 5 is shown at 59 in the lower portion of FIG. 5.

This first signature, SIGN, is adjusted in accordance with the preferred embodiment of the present invention by comparing the average value of, for example, the first signature over each pixels in length thereof. If a given value of the first signature exceeds the minimum average value of the signature over the preceding five (5) pixels by a certain clipping level, then the signature is adjusted to that minimum average value plus the clipping level.

As shown in FIG. 6, the next step 78 of the present method, after the first signature has been obtained, comprises the step of determining the first order derivatives, FD, of the first signature (SIGN) and storing those first order derivatives in an array in the memory 62. The first order derivatives FD, are preferably determined according to the following formula:

$$FD = (SIGN\ [A+1] + SIGN\ [A+2]) - (SIGN\ [A-1] + SIGN\ [A-2])$$

Other methods of determining the first order derivatives are, of course, well known and may be used.

In accordance with the preferred embodiment of the present invention, the first order derivatives FD of the first signature, SIGN, are stored in an array. This array is scanned to determine those points along the first corridor having first order derivatives typical of lead boundaries. Other first order derivatives are deleted from the array. In carrying out this technique, the microprocessor 64 scans this array for regions having first order derivatives with consecutive positive or zero values and no intervening negative values as well as for regions having consecutive negative values with no intervening positive values. Next, the first order derivative values in each such region are accumulated and summed to yield a value referred to as SUM in each such region. The local maxima in each such region is further determined and replaced with the value of the SUM of first order derivatives for that region.

In accordance with one aspect of the present invention, if two consecutive positive or two consecutive negative values of the first order derivative stored in the first array are encountered, this indicates that one of the positive first order derivatives or one of the negative first order derivatives does not define a lead boundary. Accordingly, if a first order derivative of a given element of the first array exceeds the previous element of that array by a given threshold, the previous element is set to zero in the array and the next element is adjusted to equal the sum of the derivatives of both elements.

Once the first array contains only those points along the first corridor having first order derivatives typical of lead boundaries and other first order derivatives have been deleted from that array, the next step in the lead location method of the present invention may begin. In accordance with this step, raw leads i.e., possible lead regions, are located as shown in Block 80 in FIG. 6. This is accomplished by scanning the first array to analyze those regions between suspected lead boundaries. In accordance with one aspect of the present invention, this is accomplished by scanning the first array to find the first positive value and the first negative value of the first order derivatives (FD). The regions between positive and negative first order derivatives are tentatively considered to be leads and the positions of such regions are stored in a second array in memory 62.

In accordance with the next step of the present method, after the positions of raw leads have been determined in accordance with the step shown at 80 in FIG. 6, these regions are compared against a standard which eliminates regions having a width which is less than the expected minimum width tolerance of leads of the integrated circuit package being analyzed. This step is shown at 82 in FIG. 6. In carrying out this step, the second array mentioned above is scanned to determine which of the raw lead regions has a dimension which exceeds the minimum expected dimension of the leads of the integrated circuit package being analyzed.

As shown at Decision Block 84 of the present method in FIG. 6, if the semiconductor lead frame device being analyzed is not a ceramic dual-in-line package, which therefore does not suffer from the problem of unwanted specular reflection mentioned above, the lead location operation of the present method is completed as shown at Block 86. Alternatively, however, if the package being analyzed is a ceramic dual-in-line package or cerdip, further processing must be undertaken to insure that the lead locations as determined in Steps 76-82 in fact designate leads and not specular reflections from the surface of interlead material. Accordingly, with a ceramic dual-in-line package the next step 88 of the present method is to eliminate the regions of specular reflections from consideration as leads.

In carrying out the method step shown at Block 88 of FIG. 6 of eliminating the consideration of regions of specular reflection, consideration should again be made of FIG. 5. The first step in eliminating regions of specular reflection from consideration is the conduction of an auxiliary scan in a direction orthogonal to the primary scan along corridor 57. In carrying this auxiliary scan, a series of secondary corridors are defined which are shown at 90. These second corridors each have a length l which is orthogonal to the length L of the first corridor 57 and a width w which is orthogonal to the width W of the first corridor 57. In accordance with an important aspect of the present invention, the length l of the second corridors 90 preferably exceeds the width w of the first corridor 57, whereas the width w of the second corridors 90 is very much less than the length L of the first corridor 57. Also in accordance with an important aspect of the present invention, the auxiliary scan in the aforementioned series of second corridors 90 is conducted at each possible lead boundary which has been previously determined. As shown in FIG. 5, an auxiliary scan is conducted at the leading edges 50 and 54 of the lead frame beams 16, at the trailing edges 52 and 56 of those lead frame beams as well as at the leading and trailing edges of the bright patches such as 48 and regions of specular reflection such as 46.

In accordance with an important aspect of the present invention, a second signature is computed at each corridor of the series of second corridors 90. This second signature is, again, a widthwise summation of the digital values along the length l of the second corridors 90.

Next in carrying out the method step of eliminating areas of specular reflection shown at Block 88, the three largest values of each such second signature, for example, and the three smallest values of each such signature are collected and summed. A difference (DIFF) is computed which equals the difference between the sum of, for example, the three maximum values and, for example, the sum of the three minimum values in each such corridor. This difference, DIFF, is compared against a pre-determined maximum value. If the difference is less than the pre-determined maximum value, a conclusion may be reached that the second corridor 57 is at a lead boundary and not at the leading or trailing edge of a bright patch 48 or a region of specular reflection 46.

In accordance with an alternate embodiment, the three largest, for example, and three smallest values of the second signature in each of the second corridors 90 are computed and the difference (DIFF) between the sum of the maximum values and the sum of the minimum values is computed. If this difference is less than the pre-determined maximum and further, if the first signature at the corresponding point exceeds a pre-determined minimum, a lead boundary presence such as 50, 52, 54, and 56 is confirmed. Once lead boundaries are confirmed in accordance with either of the two alternate embodiments mentioned above, the next step of the present method is to eliminate narrow leads as shown in Block 92 of FIG. 6. This is accomplished in accordance with the technique described in connection with Block 82 described above.

In accordance with both of the aforementioned embodiments, if an auxiliary scan is taken in a given second corridor and a lead boundary location is not confirmed in that auxiliary scan, another second corridor is defined immediately adjacent to the last such corridor and an auxiliary scan is conducted again. This process is repeated until a lead boundary location is confirmed.

Figure 7:
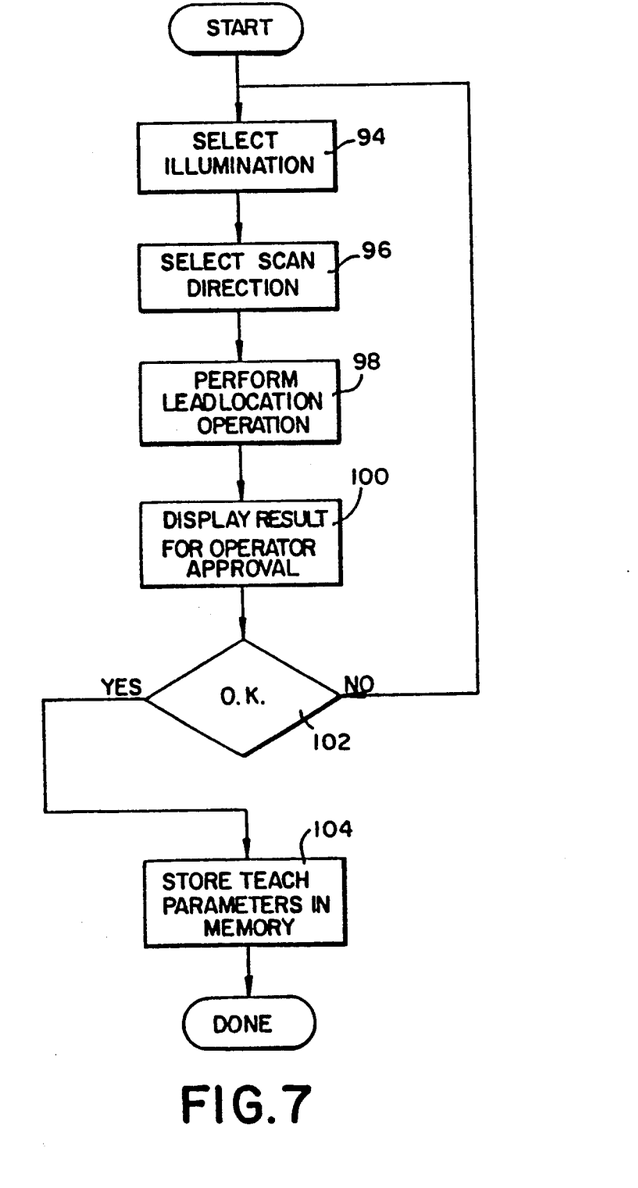
FIG. 7 is a flow chart illustrating the teach operation of the image processor of FIG. 1.

Referring now to FIG. 7, the operation of the imaging system of the present invention in a "Teach" mode will be described. Prior to the beginning of the lead location operation described in FIG. 6, the particular lead frame assembly to which wire bonds must be made is scanned in a teach operation such that the generalized parameters may be analyzed and stored. As shown in FIG. 7, the teach operation begins with the step of selecting the requisite illumination of the light source 24 as shown at Block 94. Next, the scan direction to be utilized for the definition of the first corridor 57 is determined at Block 96. A lead location operation is next performed as shown at 98, the lead location operation being conducted in accordance with the method described in FIG. 6 above. The results of the lead location operation are displayed on the monitor 38 for operator approval as indicated at Block 100. If the results are satisfactory insofar as the operator is concerned, the parameters of the standard lead frame to which bonds are to be made are stored in the memory 62. If the results are unsatisfactory as determined at Decision Block 102, the teach operation is repeated until the teach parameters are satisfactory as shown at Block 104.

Figure 8:
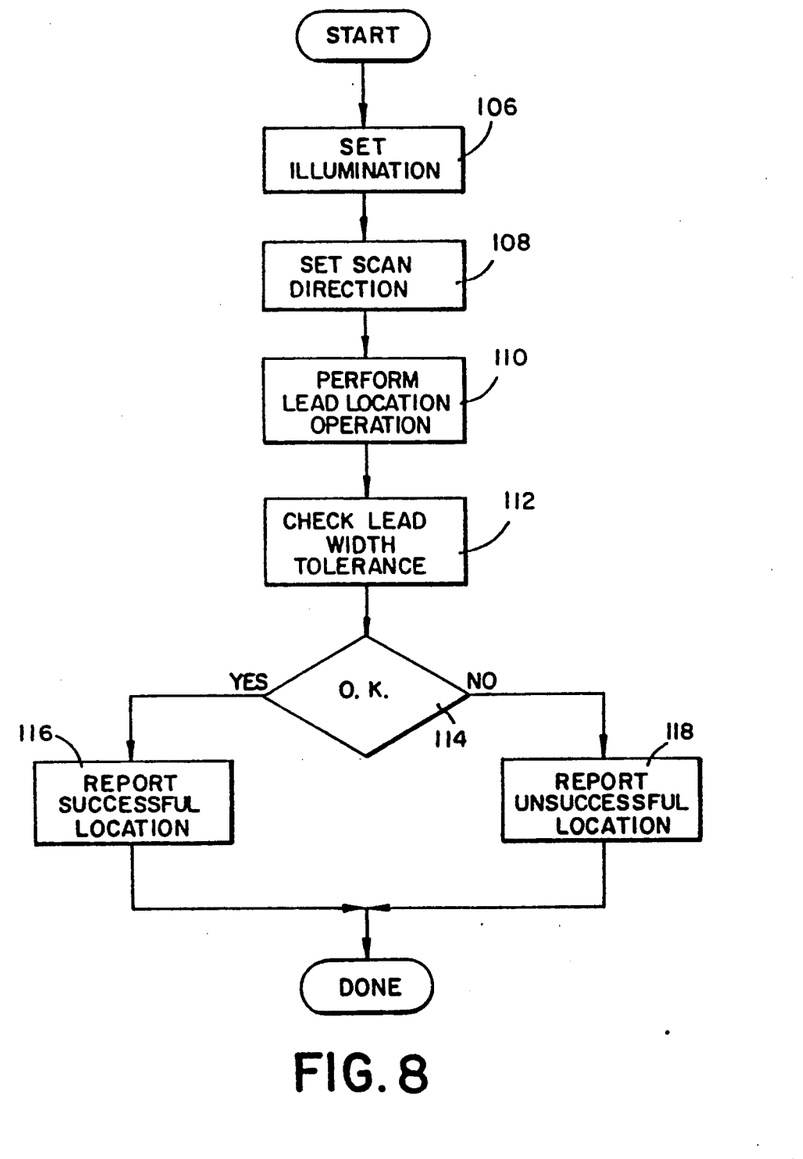
FIG. 8 is a flow chart illustrating the run operation of the image processor of FIG. 1.

As shown in FIG. 8, once the teach parameters have been stored, the operator may begin utilizing the image processing system of the present invention to locate lead frame beams and to cause automatic wire bonding thereto. In operating the image processing system of the present invention in a run mode as shown in FIG. 8, the illumination of the light source 24 is first set as shown at Block 106, the scan direction is set as shown at Block 108. Next, lead location operations following the procedure of FIG. 6 are performed as shown at Block 110. In accordance with the preferred embodiment of the present invention, once leads have been located, they may be checked as shown at Block 112 to insure that the leads are within the desired width tolerance. As shown at Decision Block 114, if the leads have been located and are within tolerance, a successful report may be displayed at monitor 38 as shown at Block 116 or an unsuccessful report may be displayed as shown at Block 118.

While a particular embodiment of the present invention has been shown and described, it will be appreciated that numerous refinements and improvements can be made to the system and method of the present invention without departure from its essential spirit and scope, which is therefore not to be construed as limited by the above exemplary disclosure, but only by the following claims:

What is claimed is:

1. A method of determining the position of leads on a semiconductor lead frame prior to making second wire bonds with a wire bonding apparatus having a pattern recognition system comprising the steps of:

illuminating said lead frame with light from a light source;

sensing light intensity levels reflected from said lead frame with said pattern recognition system;

generating digital data representing pixel intensity levels of said reflected light from a plurality of leads;

storing said pixel digital data in a memory;

defining a first corridor in said memory, said corridor having a length and a width covering a plurality of leads;

generating a signature from said digital data within said corridor along the length thereof, said signature being the widthwise summation of said pixel digital data at pixel columns along the length of said corridor;

storing said signature of the length of said first corridor in a first memory array;

scanning said first memory array to determine the points along said first corridor having signature transitions typical of lead boundaries;

deleting other signature transitions from said first array which are not typical of lead boundaries;

scanning said first memory array to determine regions between said lead boundaries typical of the allowed spacing between lead boundaries, the positions of said regions being stored in a second memory array;

scanning said second memory array to determine which of said regions have spacing exceeding the allowed dimension of properly positioned lead boundaries; and selecting pairs of lead boundaries which are typical of a lead to be wire bonded.

2. The method of claim 1 wherein said lead frame includes interlead material having a reflectivity similar to that of said leads and wherein said method further comprises the steps of:

defining a series of second corridors each having a length and a width, the length of each such second corridor being orthogonal to the length of said first corridor, each such second corridor being positioned at points along said first corridor determined to be typical of a lead boundary;

obtaining a second signature at each such second corridor, said second signature being a widthwise summation of the data along the length of said second corridor; and analyzing each of said second signatures in said second corridor to distinguish said leads from the specular reflection of light from said interlead material.

3. The method of claim 2 wherein the length of each such second corridor exceeds the width of said first corridor, and wherein the width of said second corridor is smaller than the length of said first corridor.

4. The method of claim 3 wherein said analyzing step further comprises:
   determining the differences between the maxima and the minima of each said second signature of said series of second signatures; and
   comparing each of said differences with a pre-determined maximum, the location of a lead boundary being confirmed whenever a given difference is less than said pre-determined maximum.

5. The method of claim 3 wherein said analyzing step further comprises:
   determining the difference between the maxima and the minima of each second signature of said series of second signatures;
   comparing each of said differences with a pre-determined maximum; and
   comparing the first signature value at each point typical of a lead boundary with a pre-determined minimum, the location of a lead boundary being confirmed whenever the difference between the maxima and the minima of a given second signature is less than said pre-determined maximum and the corresponding first signature value exceeds said minimum.

6. The method of either of claims 4 or 5 further comprising the step of:
   comparing the dimension of adjacent lead boundaries with a pre-determined dimension, a lead being precisely located whenever said pre-determined dimension is exceeded.

7. A method of determining the position of leads on a semiconductor lead frame comprising the steps of:
   illuminating said lead frame with light from a light source;
   sensing light intensity levels reflected from said lead frame;
   generating a digital data set representing pixel intensity levels of said reflected light from a plurality of leads;
   defining a first corridor in said data set, said first corridor having a length and width covering a plurality of leads;
   generating a first signature of said data set within said corridor along the length thereof, said signature being the widthwise summation of said pixel digital data at pixel columns along the length of said corridor;
   determining the first order derivatives of said first signature and storing said first order derivatives in one array;
   scanning said one array to determine the regions along the length of said corridor having the general characteristics of leads;
   storing the positions of said regions in another array; and
   scanning said another array to determine which of said regions have a dimension exceeding the minimum dimension of leads.

8. The method of claim 7 wherein said lead frame includes interlead material having reflectivity similar to that of said leads and wherein said method comprises the additional steps of:
   defining a second corridor having a length and a width, the length of said second corridor being orthogonal to the length of said first corridor;
   obtaining a second signature of said data set in said second corridor along the length thereof at each of the boundaries of each of said regions;
   analyzing each of said second signatures in said second corridor to distinguish lead boundaries from the specular reflection of light from said interlead material.

9. The method of claim 8 wherein said analyzing step further comprises:
   determining the differences between the maxima and the minima of each of said second signatures; and
   comparing each of said differences with a pre-determined maximum, a lead boundary being distinguished from specular reflection whenever said difference is less than said pre-determined maximum.

10. The method of claim 8 wherein said analyzing step further comprises:
    determining the differences between the maxima and the minima of each of said second signatures;
    comparing each of said differences with a pre-determined maximum; and
    comparing the first signature value at each of said region boundaries with a pre-determined minimum, a lead boundary being distinguished from specular reflection whenever said difference is less that said pre-determined maximum and said first signature value exceeds said pre-determined minimum.

11. The method of either of claims 9 or 10 further comprising the step of:
    comparing the dimension between adjacent lead boundaries with a pre-determined dimension, a lead being located whenever said pre-determined dimension is exceeded.

12. The method of claim 7 further comprising the step of:
    storing said digital data set in a memory, said first corridor being defined in said memory.

13. A method of determining the position of leads on a semiconductor lead frame with respect to a wire bonding apparatus comprising the steps of:
    illuminating said lead frame with light from a light source;
    sensing light intensity levels reflected from said lead frame;
    generating digital data representing pixel intensity levels of said reflected light from a plurality of leads;
    storing said pixel digital data in a memory;
    defining a first corridor in said memory, said corridor having a length and a width covering a plurality of leads;
    generating a first signature of said data within said corridor along the length thereof, said first signature being the widthwise summation of said pixel digital data at pixel columns along the length of said corridor;

determining the location of candidate lead boundaries from said first signature by analyzing the changes in said first signature along the length of said corridor and storing said locations in a first array;

scanning said first array to determine regions between said candidate lead boundaries typical of leads, the positions of said regions being stored in a second array; and scanning said second array to determine which of said regions have a dimension exceeding the minimum dimension of leads.

14. The method of claim 13 wherein said lead frame includes interlead material having a reflectivity similar to that of said leads and wherein said method further comprises the steps of:

defining a series of second corridors each having a length and a width, the length of each such second corridor being orthogonal to the length of said first corridor, each such second corridor being positioned at points along said first corridor determined to be typical of a lead boundary;

obtaining a second signature at each such second corridor, said second signature being a widthwise summation of the data along the length of said second corridor; and analyzing each of said second signatures in said second corridor to distinguish said leads from the specular reflection of light from said interlead material.

15. The method of claim 14 wherein the length of each such second corridor exceeds the width of said first corridor, and wherein the width of said second corridor is smaller than the length of said first corridor.

16. The method of claim 15 wherein said analyzing step further comprises:

determining the differences between the maxima and the minima of each said second signature of said series of second signatures; and comparing each of said differences with a pre-determined maximum, the location of a lead boundary being confirmed whenever a given difference is less than said pre-determined maximum.

17. The method of claim 14 wherein said analyzing step further comprises:

determining the difference between the maxima and the minima of each second signature of said series of second signatures;

comparing each of said differences with a pre-determined maximum; and comparing the first signature value at each point typical of a lead boundary with a pre-determined minimum, the location of a lead boundary being confirmed whenever the difference between the maxima and the minima of a given second signature is less than said pre-determined maximum and the corresponding first signature value exceeds said minimum.

18. The method of either of claims 16 or 17 further comprising the step of:

comparing the dimension of adjacent lead boundaries with a pre-determined dimension, and means a lead being precisely located whenever said pre-determined dimension is exceeded.

19. An image processing system for determining the position of leads on a semiconductor lead frame for use with a wire bonding apparatus comprising:

a light source for illuminating said lead frame;
means for sensing light intensity levels reflected from said lead frame;

means, responsive to said sensing means, for generating digital data representing pixel intensity levels of said reflected light from a plurality of leads;

memory means, responsive to said generating means, for storing said pixel digital data, said memory means including a first and a second memory array;

control means for defining a first corridor in said memory means, said corridor having a length and a width covering a plurality of leads, for generating a signature from said digital data within said corridor along the length thereof, said signature being the widthwise summation of said pixel digital data at pixel columns along the length of said corridor, for determining the locations of candidate lead boundaries from said signature by analyzing the changes in said signature along the length of said corridor, and for storing said locations in said first array, said control means further including means for scanning said first array to determine regions between said candidate lead boundaries typical of leads and for storing the position of said regions in a said second array, said second array being scanned by said control means to determine the position of said leads by determining which of said regions have a dimension exceeding the allowed dimension of leads.

20. A method of determining the actual position of a lead on a lead frame prior to bonding a fine wire thereon employing an automatic fine wire bonder of the type equipped with an improved pattern recognition system, comprising the steps of:

illuminating a plurality of leads of a lead frame including the lead from a lead to be bonded and leads adjacent thereto;

sensing the analog pixel intensity levels from said plurality of lead frame leads;

converting said analog pixel intensity levels to digital data;

storing said digital data representative of said pixels in a memory map;

combining columns of digital pixel data to provide a one dimensional digital signature;

determining the location of candidate lead boundaries by detecting large differential changes in adjacent columns of digital pixel data of said signature;

storing the location of candidate lead boundaries in a first memory array; and comparing the distance between candidate lead boundaries with data representative of ideal predetermined distances between lead boundaries, and selecting the two unique lead boundaries from lead boundaries representative of a plurality of leads that fall within predetermined portion of said signature as the lead boundaries and the location of the lead boundaries of the actual lead to be bonded.

21. The method of claim 20 wherein the step of determining the location of candidate lead boundaries comprises the step of adding a plurality digital pixel values in columns of rows of pixels to obtain said one dimensional digital signature, and taking a first order derivative of said one dimensional signature to provide slope change of intensity levels indicative of said lead boundaries.

22. The method of claim 20 wherein said step of determining the location of candidate lead boundaries further includes the step of:

setting threshold differential change values for candidate lead boundaries; and eliminating candidate lead boundaries that fall below said threshold values.

* * * * *